United States Patent [19]

Spotorno

[11] Patent Number: 4,728,334
[45] Date of Patent: Mar. 1, 1988

[54] SHAFT FOR HIP JOINT PROSTHESIS
[75] Inventor: Lorenzo Spotorno, Ligure, Italy
[73] Assignee: Protek AG, Bern, Switzerland
[21] Appl. No.: 903,854
[22] Filed: Aug. 29, 1986

Related U.S. Application Data
[63] Continuation of Ser. No. 644,533, Aug. 27, 1984, abandoned.

[30] Foreign Application Priority Data

Aug. 29, 1983 [DE]  Fed. Rep. of Germany ....... 3331162

[51] Int. Cl.⁴ ............................................... A61F 2/32
[52] U.S. Cl. ..................................................... 623/23
[58] Field of Search .............................. 623/16, 22, 23

[56] References Cited

U.S. PATENT DOCUMENTS
2,719,522 10/1955 Hudack .
2,781,758 2/1957 Chevalier ....................... 128/92 CA

FOREIGN PATENT DOCUMENTS
41591 2/1981 European Pat. Off. .............. 623/23
0027160 4/1981 European Pat. Off. .
0058745 9/1982 European Pat. Off. .
0093378 11/1983 European Pat. Off. .
2324865 11/1974 Fed. Rep. of Germany ........ 623/23
2356464 5/1975 Fed. Rep. of Germany .
2627569 12/1977 Fed. Rep. of Germany .
2537807 2/1980 Fed. Rep. of Germany .
8213101 8/1982 Fed. Rep. of Germany .
560042 3/1975 Switzerland .......................... 623/23

Primary Examiner—Richard J. Apley
Assistant Examiner—David J. Isabella
Attorney, Agent, or Firm—Toren, McGeady & Associates

[57] ABSTRACT

In a femur component of a hip joint prosthesis, a straight shaft member is formed at least over the length of a proximal portion thereof located at the proximal end of the shaft member with a conical configuration which widens taken in a direction toward the proximal end of the shaft member and with a narrowing configuration taken from the lateral side to the medial side of the shaft member.

16 Claims, 3 Drawing Figures

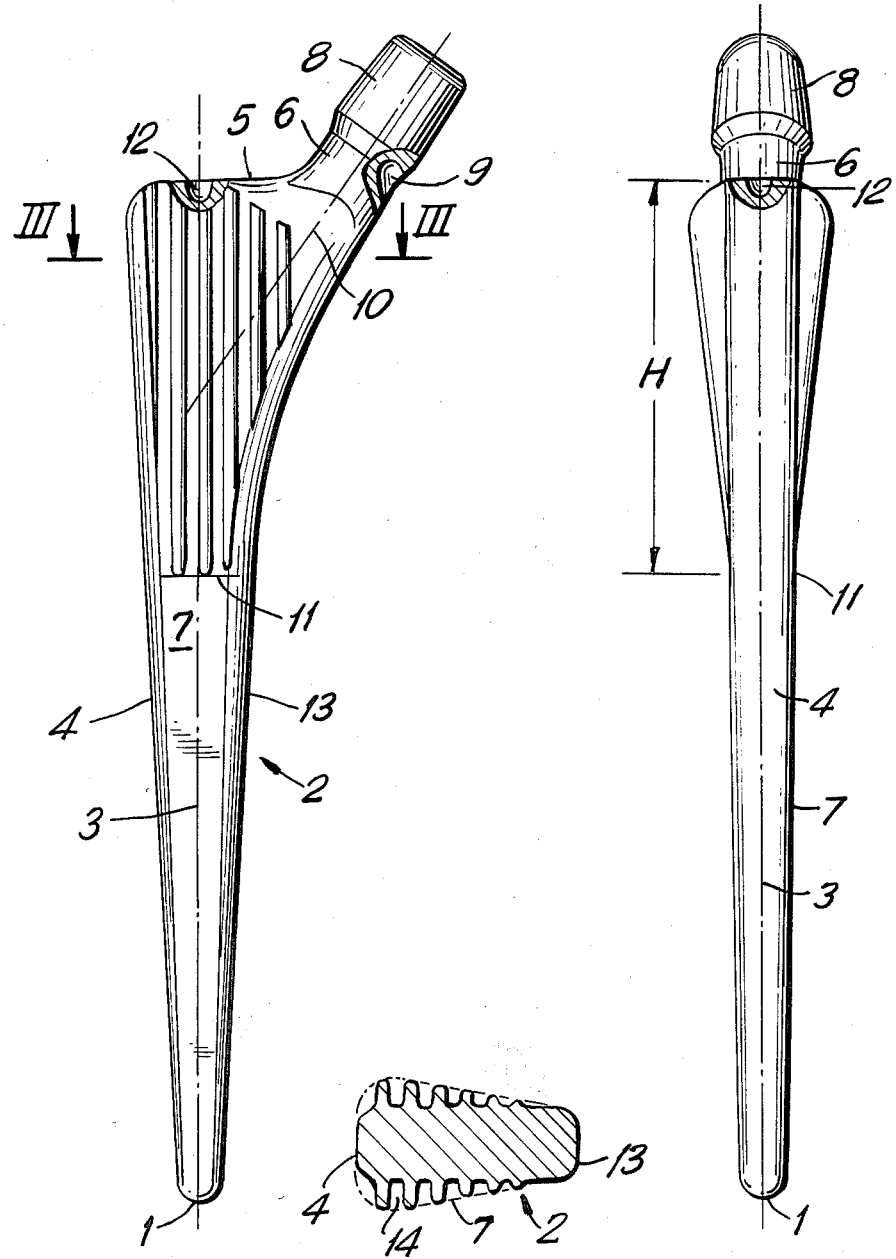

SHAFT FOR HIP JOINT PROSTHESIS this is a continuation of application Ser. No. 644,533 filed Aug. 27, 1984 now abandoned.

The present invention relates generally to prosthesis devices and more specifically to the structure of a femur component of a hip joint prosthesis. More specifically, the prosthesis device of the invention basically involves a construction formed as a straight shaft which conically widens about the entire periphery thereof taken from its distal end.

A femur component for a hip joint prosthesis of the type to which the present invention relates is known in the prior art from U.S. Pat. No. 2,719,522 wherein there is disclosed a device having a shaft in the form of a truncated cone which widens continuously from the distal end to the proximal end. Furthermore, this shaft has an addititional conical widening with a circular cross-section in the proximal shaft area.

A shape of this type is only approximately capable of being adjusted to the proximal narrow space of the femur. However, such a shape does not result in optimum anchoring in the proximal area which is of particular importance for prosthesis shafts which are to be implanted without the use of cement.

It has also been found in recent years that hip joint prostheses settle after a period of time, i.e., they tend to sink deeper into the bone. Thus, it is important that, during this sinking, the prosthesis immediately again locks and fastens so that at the boundary surface of the prosthesis, or of the cement bed to the bone, no micromovements occur which could lead to bone removal, as is well known.

The prosthesis shaft described in U.S. Pat. No. 2,719,522 enables relocking only during axial sinking of the prosthesis shaft. However, it has been found that sinking of the prosthesis shaft does not occur only in the direction of the longitudinal axis of the shaft, but that, due to the moment which is exerted by the stress acting on the joint head of the femur component with regard to the longitudinal axis, a medially directed sinking, particularly in the proximal area of the shaft does occur.

Accordingly, the present invention is directed toward a device which is particularly concerned with correcting for this occurrence.

SUMMARY OF THE INVENTION

Briefly, the present invention may be defined as a femur component of a hip joint prosthesis which comprises a straight shaft member wherein the shaft member is formed, at least over a length dimension which extends near the proximal end of the shaft, with a conical configuration which widens taken in the direction toward the proximal end of the shaft and with a configuration which narrows laterally taken from the lateral side to the medial side of the shaft.

Accordingly, the invention operates to provide a solution to the aforementioned problems which result with prior art prostheses by creating a femur component of a hip joint which, due to its construction, is shaped with multiple conical portions and which makes possible anchoring primarily in the proximal part of the shaft. The structural configuration of the invention also particularly secures the prosthesis in the medial direction particularly in the case of settling movement of the prosthesis shaft thereby providing a basically new fixation characteristic which acts as rapidly as possible.

The advantages achieved with the invention arise essentially due to the fact that the shaft, during yielding in the medial direction, as well as during settling movement in the direction of the longitudinal axis, immediately again locks and fastens so that due to the shaft tapering which extends from the lateral to the medial side an optimum transfer of torsional forces is achieved.

The absorption of torsional forces in the proximal shaft area may be further improved in that provision is made for groovelike recesses which extend essentially in the direction of the longitudinal axis of the shaft along the length of the shaft at the proximal end. However, under certain circumstances, it is advantageous to form the groove-shaped recesses so as to extend essentially in the direction of the main bar courses of the spongiosa structure surrounding the shaft. The pronounced axial rib structure makes it possible for the spongiosa structure of the femur to be included in the form-locking of the prosthesis shaft.

The present invention is adapted to utilize all materials which are used for prosthesis shafts for endoprosthesis, and titanium alloy is particularly suitable.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there is illustrated and described a preferred embodiment of the invention.

DESCRIPTION OF THE DRAWINGS

In the drawings:

FIG. 1 is a front view showing a prosthesis shaft in accordance with the invention;

FIG. 2 is a left side view of the shaft shown in FIG. 1; and

FIG. 3 is a sectional view taken along the line III—III of FIG. 1.

DETAILED DESCRIPTION OF A PREFERRED EMBODIMENT

Referring now to the drawing wherein there is shown a preferred embodiment of the invention, it will be seen that the present invention essentially consists of a blade member or shaft member 2 which forms a femur component of a hip joint prosthesis. The shaft member 2 is formed with a conical configuration which widens symmetrically relative to a longitudinal center axis 3 beginning from a distal end 1 of the shaft 2. The shaft 2 comprises a lateral narrow side 4 which ends in an almost horizontal shoulder 5 which forms a transition extending to a prosthesis neck 6. In the shoulder 5, concentrically with the longitudinal center axis 3 of the shaft 2, there is provided a recess 12 for application of an insertion instrument for driving in the prosthesis.

The shaft 2 also is formed with a medial side 13, which is narrower than the lateral side 4 and with side flanks or blade sides 7. The widening cone of the medial narrow side 13 of the side flanks or blade sides 7 changes over to a circular arc which ends without steps in the prosthesis neck 6. The latter carries a pin 8 onto which a joint head (not shown) may be placed. The CCD-angle is 145°.

At the underside of the prosthesis neck 6, there is an additional recess 9 and, in this recess, a removal instrument may be inserted, if necessary.

Referring to FIGS. 2 and 3, it will be seen that the longitudinal axis 3 and the axis 10 of the prosthesis neck 6 define a center plane of the shaft 2 which, at the same time, is a plane of symmetry of the shaft 2.

At the distal end 1, the narrow sides 4 and 13 and the blade sides 7 are closed by means of a semi-ellipsoidal transition.

As seen in FIG. 2, not only do the blade sides 7 widen, taken from the distal end 1, although the generating angle is relatively small and is, for example, 0.5° to 3° towards the vertical.

As FIG. 2 clearly shows, the conical widening configurations of the blade sides 7 which, in the inserted prosthesis, point toward the anterior or posterior, have a discontinuity or transition part 11. Taken from this discontinuity or transitional part, and extending toward the proximal end, the opening or cone angle formed by the blade sides 7 with the center plane or plane of symmetry of the shaft is enlarged. Although, in the shaft 2 shown in the drawings, this opening or cone angle is approximately 1.5° in the distal area, its value in the proximal area is between 4° and 10° and preferably between 6° and 8°. In the embodiment shown in the drawings, this angle is approximately 7°.

The proximal area of the shaft 2, which is widened in this manner and reinforced, forms in its cross-sectional configuration, as seen in FIG. 3, an equilateral trapezoid whose corners are rounded off. From the relatively wide lateral side 4, the cross-section narrows symmetrically to the center plane of the shaft toward the medial narrow side 13 so that the blade sides 7 form a third cone. Its angle toward the center plane may be between 5° and 20° and preferably between 10° and 15°.

As already described, this cone makes a rapid fastening of the prosthesis possible when the prosthesis settles some time after its implantation, i.e., when, with a pitching motion of the joint head, it yields to possible occurrences involving reactions of the bone to the foreign body which the prosthesis represents.

The shaft 2 is formed with a proximal range H of the blade sides or side flanks 7 which is provided with grooves or recesses 14, best seen in FIG. 3, which are arranged in such a manner that the base sides of the grooves or recesses 14 extend approximately parallel to the implantation direction of the implant which coincides with the direction of the longitudinal center axis 3. The grooves or recesses 14 which have a minimum depth of 1 mm, and preferably a depth of 2 mm, operate to ensure an anchoring and fixation of the shaft as far proximally as possible, particularly in a prosthesis which is to be implanted without cement and to primarily transfer the bending and torsional stresses which act on the shaft 2 onto the bones. The recesses 14 can, for example, be manufactured in metal shafts by cutting with the aid of a form cutter which has a profile corresponding to the recesses 14.

The distances of the grooves or recesses should be 2 to 8 mm, and preferably between 3 and 6 mm. This structure results in a considerable enlargement of the surface of the prosthesis shaft which comes into contact with the bone and consequently there occurs a tight anchoring which, together with the multiple cone shape, ensures optimum anchoring in the proximal area of the femur. The surface enlargement is, advantageously, 1.3 to 2.7 times, and preferably between 1.6 and 2.4 times, the unstructured surface.

In the distal area of the femur component, a surface structure was intentionally omitted in order not to prevent secondary fixation due to sinking.

While a specific embodiment of the invention has been shown and described in detail to illustrate the application of the inventive principles, it will be understood that the invention may be embodied otherwise without departing from such principles.

What is claimed is:

1. In a femur component of a hip joint prosthesis consisting essentially of a straight shaft member defining a longitudinal axis, having a distal end, a proximal end, an anterior side, a posterior side, a medial side and a lateral side, said shaft member widening conically from said distal to said proximal end and from said medial to said lateral side, the improvement comprising said shaft member having in a proximal portion a plurality of distinct blades, having recesses therebetween wherein said blades and resecces are disposed substantially parallel to said longitudinal axis, each said blade having a broad surface extending a distance perpendicularly to the anterior posterior plane of said shaft and wherein said distance and depth of each of said blade and recess increases in a direction from said medial to said lateral side to yield a generally conical configuration; and said recesses between said blades having a depth which gradually decreases in a direction from said lateral to said medial side.

2. A femur component according to claim 1, wherein said shaft member is formed with a transitional portion at the distal end of said proximal range H, said femur component being formed with recesses extending in said proximal range H on said side flanks proximal to said transitional portion.

3. A femur component according to claim 1, wherein said shaft member comprises a longitudinal center axis and wherein said recesses extend essentially in the direction of said center axis.

4. A femur component according to claim 1, wherein in said proximal range H said anterior and posterior sides are formed with a conical configuration which extends at a cone angle of between 4° and 10°.

5. A femur component according to claim 4, wherein said cone angle is between 6° and 8°.

6. A femur component according to claim 1, wherein in said proximal range H said shaft member has a narrowing configuration from said lateral side to said medial side shaped with a cone angle of between 5° and 20°.

7. A femur component according to claim 6, wherein said cone angle is between 10° and 15°.

8. A femur component according to claim 1, wherein said recesses are formed with a minimum depth of 1 mm.

9. A femur component according to claim 8, wherein the depth of said recesses is 2 mm.

10. A femur component according to claim 1, wherein said recesses extend over a distance of between 2 and 8 mm.

11. A femur component according to claim 10, wherein said recesses extend over a distance of between 3 and 6 mm.

12. A femur component according to claim 1, wherein the exposed surface area of said shaft member in said proximal range H is enlarged by the formation of said recesses by a factor of between 1.3 and 2.7 times.

13. A femur component according to claim 12, wherein said surface area is enlarged by a factor of between 1.6 and 2.4 times.

14. A femur component according to claim 1, wherein said shaft member at said proximal range H has a cross-sectional configuration which is in the shape of a trapezoid.

15. A femur component according to claim 14, wherein said cross-sectional configuration of said proximal range H is in the shape of an equilateral trapezoid.

16. A femur component according to claim 1, wherein said shaft member has a smooth surface extending along the distal part thereof from said transitional portion to said distal end.

* * * * *